(12) United States Patent
Ganguli et al.

(10) Patent No.: US 8,741,435 B2
(45) Date of Patent: Jun. 3, 2014

(54) METHOD AND APPARATUS FOR COATING SUBSTRATES

(75) Inventors: Rahul Ganguli, Thousand Oaks, CA (US); Tony Ten-Luen Liao, South Pasadena, CA (US); Roberto S. Santos, Hudson, MA (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 445 days.

(21) Appl. No.: 12/772,007

(22) Filed: Apr. 30, 2010

(65) Prior Publication Data

US 2011/0268974 A1 Nov. 3, 2011

(51) Int. Cl.
*B32B 27/00* (2006.01)
*A01N 59/16* (2006.01)
*B32B 27/18* (2006.01)

(52) U.S. Cl.
USPC .......................................... 428/422

(58) Field of Classification Search
None
See application file for complete search history.

(56) References Cited

U.S. PATENT DOCUMENTS

| | | | |
|---|---|---|---|
| 4,766,188 A * | 8/1988 | Attwood et al. | 526/227 |
| 6,054,504 A | 4/2000 | Dalla Riva Toma | |
| 6,093,407 A | 7/2000 | Cummings et al. | |
| 6,432,416 B1 | 8/2002 | Cummings et al. | |
| 7,107,100 B2 * | 9/2006 | Imran et al. | 607/40 |
| 2005/0025800 A1 * | 2/2005 | Tan | 424/423 |
| 2006/0134404 A1 * | 6/2006 | Witsch | 428/331 |
| 2006/0182981 A1 * | 8/2006 | DeBergalis et al. | 428/473 |

OTHER PUBLICATIONS

Markarian, New developments in antistatic and conductive additives, Plastics, Additives and Compounding, Sep. 23, 2008, vol. 10, Issue 5, pp. 22-25.*
Hummers et al., Preparation of Graphitic Oxide, William S., Journal of the American Chemical Society, 1958, vol. 80, p. 1339.*
AgION, AgION Technologies, Inc., Technical Data, retrieved Nov. 20, 2012, pp. 1-4, http://www.harmsco.com/agiont.pdf.*
Chen et al., Preparation and characterization of graphite nanosheets from ultrasonic powdering technique, College of Materials Science and Engineering, Huaqiao University, 2004, pp. 753-759.*
E2F-D Anti-Microbial Inductive Sensors; Proximity Sensors with FDA-Approved Bacteria Inhibiting Housing Reduces Risk of Food Contamination; 2006 Omron electronics LLC.
Ensinger Reduces the Risk of Food Contamination; Omron Industrial Automation.
http://www.agion-tech.com/markets.aspx?id=50; Electronics Customers; List of Companies with Anti-Microbial Products.
Carbon Steel; McMaster-Carr-Catalog.
Cole-Parmer Catalog; 2009-2010.
New Omron E2F-D Proximity Sensor Features an Anti-Bacterial Housing to Help Fight Risk of In-Process Contamination.
E2F-D Proximity Sensor with Nanotechnology; Product News; http://www.omron-ap.com/news_center/product26.htm.
MSC Catalog; Antimicrobial Single Barb Tube Fitting; p. 3992.
Surface Bonded Antimicrobial Coatings; Solvent & Water Based; Hydromer.
www.dupontpowder.com; Alesta AM: Antimicrobial-treated Powder Coatings; last viewed Aug. 10, 2009 (4 pages).

* cited by examiner

*Primary Examiner* — Callie Shosho
*Assistant Examiner* — Patrick English
(74) *Attorney, Agent, or Firm* — Fletcher Yoder, P.C.

(57) ABSTRACT

According to various embodiments, a coating mixture is capable of being applied on a substrate. The coating mixture includes acidified graphite particles, a suspension of polytetrafluoroethylene resin in water, and silver ion doped microporous particles. When the coating mixture is applied to a surface of the substrate, the coating resists growth of microorganisms.

24 Claims, 4 Drawing Sheets

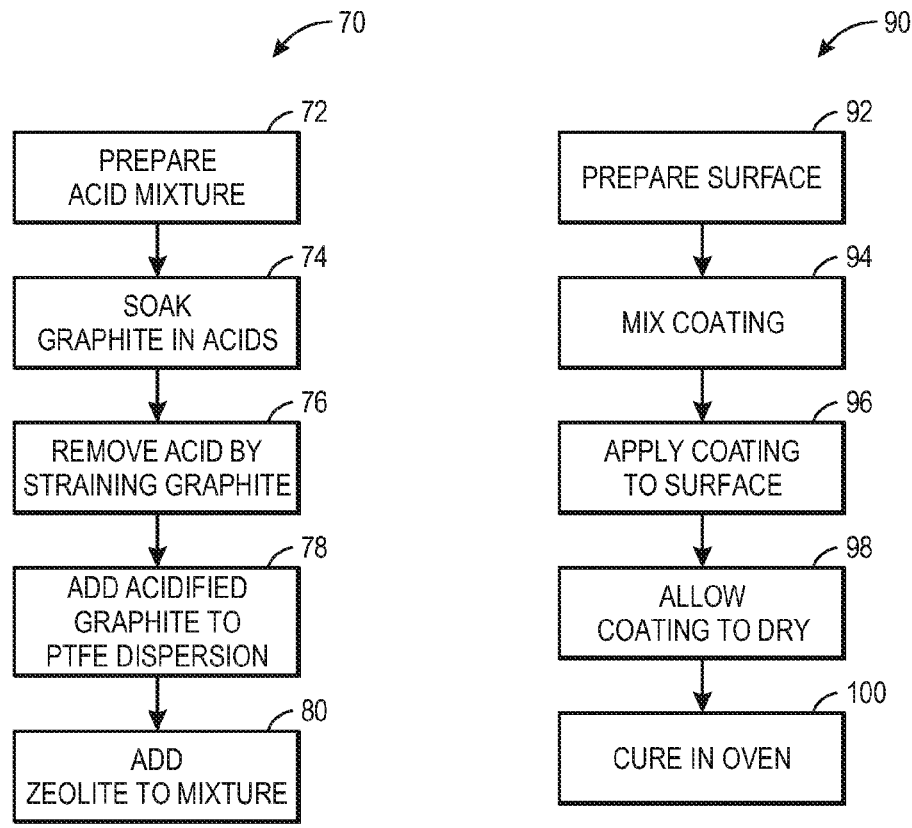
FIG. 5
FIG. 6
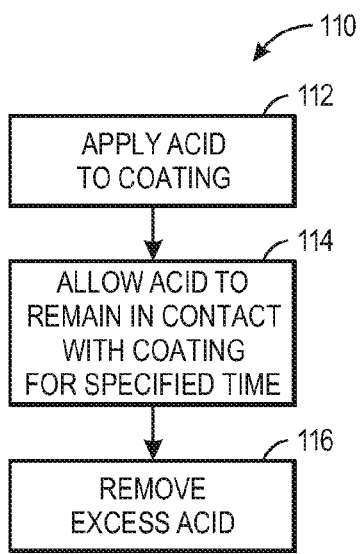
FIG. 7

METHOD AND APPARATUS FOR COATING SUBSTRATES

BACKGROUND

The invention relates generally to protective systems, and, more particularly, to antimicrobial coatings.

In many industries, equipment may be exposed to a variety of conditions and contaminants during use. For example, in the food industry, equipment may become dirty or contaminated with microorganisms. Thus, equipment may be cleaned to reduce the risk of uncontrolled growth of microorganisms. Cleaning methods may include the use of high-pressure water sprays. Where high-pressure water alone is inadequate to remove debris, mechanical methods of removal may be used. Mechanical methods, such as scraping, grinding, or brushing, may scratch and damage surfaces because of the repeated mechanical contact. In addition, a variety of chemicals may be used in conjunction with high-pressure water and mechanical methods. These chemicals may be corrosive or damaging to some materials. Surfaces missed by any of these methods or not cleaned sufficiently may continue to harbor viable microorganisms.

BRIEF DESCRIPTION

The present invention provides novel techniques for protecting substrates with a non-stick, water-based, antimicrobial coating. In particular, the present techniques are presented in the context of the food industry, where such a coating may be beneficial in addressing issues regarding durability, ease of cleaning, and microorganism growth. More particularly, the invention may be very beneficial to preventing, slowing or limiting microbial growth on equipment in such settings. However, it should be borne in mind that the invention may be applied in a wide range of contexts, on a variety of substrates, and in any desired industrial, commercial, private, or other environment.

In accordance with one aspect of the present disclosure, a coating mixture is capable of being applied on a substrate. The coating mixture includes acidified graphite particles, a suspension of polytetrafluoroethylene (PTFE) resin in water, and silver ion doped microporous particles. When the coating mixture is applied to a surface of the substrate, the coating resists growth of microorganisms.

In accordance with another aspect, a method of manufacturing an antimicrobial coating includes adding a slurry of acidified graphite particles to a suspension of PTFE resin particles in water, adding silver ion doped microporous particles to the mixture of the acidified graphite particles and the suspension of PTFE resin particles in water, and mixing until the coating is homogeneous.

In accordance with a further aspect, a method of covering a substrate with an antimicrobial coating includes preparing the substrate by roughening a surface of the substrate and mixing the coating until the coating is homogenous. The coating includes acidified graphite particles, PTFE resin particles, silver ion doped microporous particles, and water. Further steps of the method include applying the coating to the surface of the substrate, allowing the coating to dry, and curing the coating at a temperature greater than a melting point of the PTFE resin particles.

In accordance with still another aspect, a coated sensor includes a sensor and an antimicrobial coating covering a surface of the sensor. The coating includes acidified graphite particles, PTFE resin particles, and silver ion doped microporous particles.

In accordance with yet another aspect, a method of reactivating an antimicrobial coating covering an article includes applying an acid to the surface of the coating. The coating includes acidified graphite particles, PTFE resin particles, and silver ion doped microporous particles. Further steps of the method include allowing the acid to remain in contact with the surface of the coating for a time sufficient to reactivate the antimicrobial coating, and removing excess acid from the surface of the coating.

DRAWINGS

These and other features, aspects, and advantages of the present invention will become better understood when the following detailed description is read with reference to the accompanying drawings in which like characters represent like parts throughout the drawings, wherein:

FIG. 5 is a flowchart of an exemplary method for preparing a non-stick, water-based, antimicrobial coating;

FIG. 6 is a flowchart of an exemplary method for applying a non-stick, water-based, antimicrobial coating to a surface of an object; and FIG. 7 is a flowchart of an exemplary method for reactivating a non-stick, water-based, antimicrobial coating.

DETAILED DESCRIPTION

A variety of equipment in a number of industries may be exposed to microorganisms during use. Examples of such industries include, but are not limited to, the food, beverage, fiber and textile, household and personal care, and life science industries. In the food industry, for example, equipment that may be exposed to microorganisms includes sensors, belts, programmable logic controllers, drives, power transmission components, safety products, and industrial automation devices. Such equipment may be exposed to raw animal and plant components or other ingredients that may possibly contain microorganisms. Microorganisms may be viable and continue to reproduce on the surfaces of the equipment. In addition, the heat and humidity common to much of the food industry may further facilitate the growth of bacteria, molds, mildews, and other microorganisms. Thus, hygienic food practices include cleaning and sanitization of surfaces in contact with or likely to be exposed to food and other sources of microorganisms. These practices may involve use of high pressure and chemicals, such as detergents, surfactants, acids, bases, and sanitizers. Such practices may contribute to damage of equipment surfaces. In addition, higher pressure washes or mechanical removal that may further harm equipment may be used when food and other debris cannot be removed easily. Finally, uneven, inadequate, or improper cleaning may leave some microorganisms alive to further grow and multiply.

In the particular embodiments described below, a non-stick, water-based, antimicrobial coating may be applied to food equipment, such as, in an exemplary embodiment discussed in detail, sensors, to reduce the effects described above. The hardness of certain embodiments of the coating may help the coating endure high-pressure washes, abrasions, and scratches without physical damage, such as peeling, flaking, or cracking. In addition, the non-stick qualities of other embodiments may help food, debris, and microbes to be able to be more easily washed or removed from equipment. Finally, the antimicrobial qualities of further embodiments may help kill any microbes that are exposed to the coating.

Figure 1:
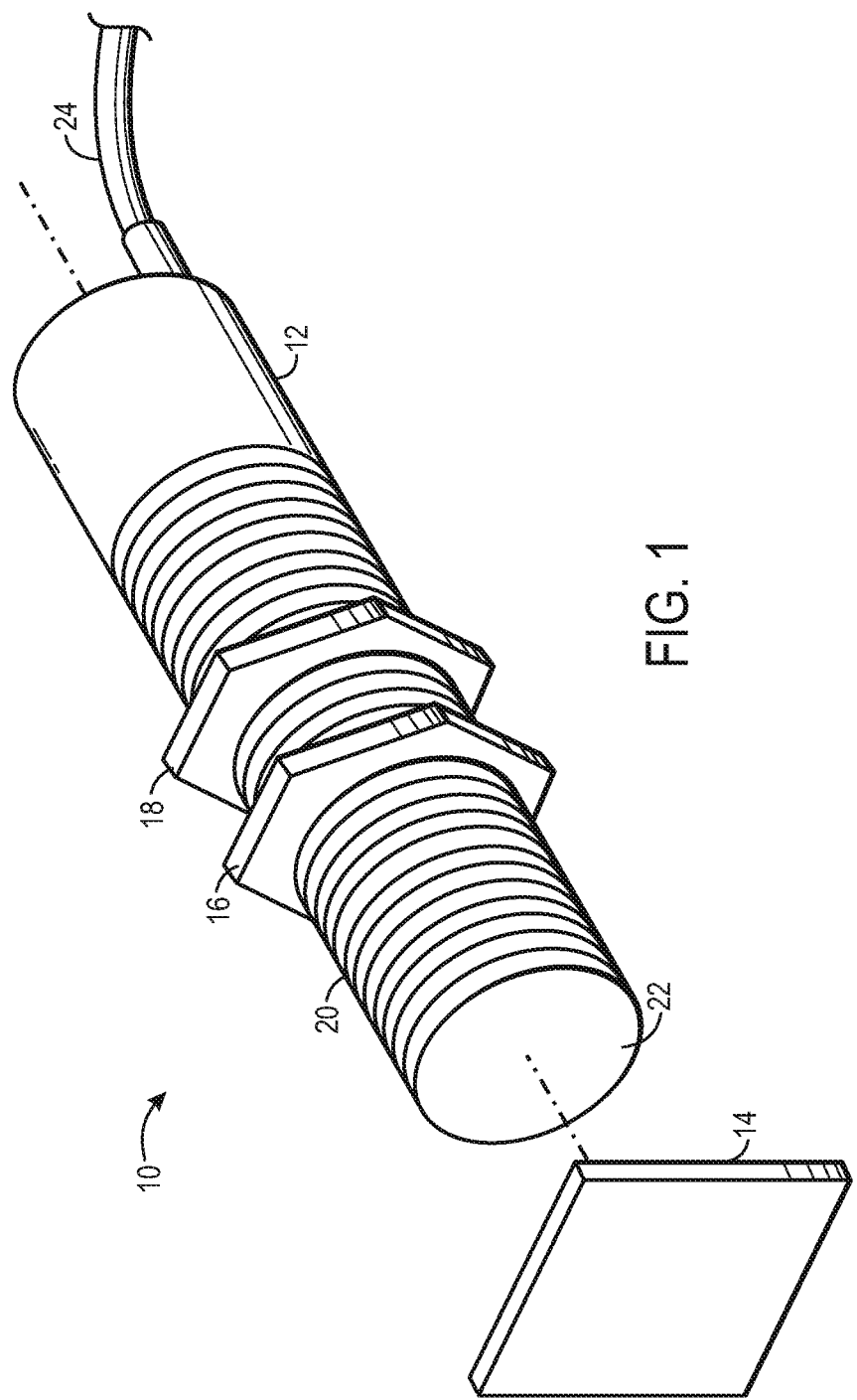
FIG. 1 is a perspective diagram of an exemplary sensor system, presented here as one possible device or substrate on which the new antimicrobial coating may be applied.

With the foregoing considerations in mind, FIG. 1 is a perspective diagram of a proximity sensor system 10 in accordance with an embodiment of the present disclosure. Examples of proximity sensor technologies include, but are not limited to, inductive, capacitive, and ultrasonic. In addition, other types of sensors may be coated, such as photoelectric sensors, encoders, and limit switches, as well as other industrial automation devices, such as controllers, push buttons, or cordsets. Returning to FIG. 1, a sensor body 12 may include the electronics and other components necessary to be able to detect a nearby object 14, commonly referred to as a target. For example, the sensor body 12 may emit an electromagnetic field or emit a beam of electromagnetic radiation. Subsequently, the sensor body 12 may detect changes in the field or detect a return signal. First and second mounting flanges 16 and 18 may be used to secure the sensor body 12 to an object, such as a mounting bracket. The flanges 16 and 18 may be threaded to couple with threads 20 provided on the surface of the sensor body 12. Thus, the sensor body 12 may be inserted through a hole in the mounting bracket and the flanges 16 and 18 tightened against opposite sides of the bracket to secure the sensor body. The sensor body 12 may be configured such that a face 22 is directed toward the target 14. The field or beam from the sensor body 12 may be configured to primarily be directed through the face 22. Finally, a cable 24 may be coupled to the sensor body 12 away from the face 22. The cable 24 may provide power for the sensor body 12 and enable for remote operation.

Regarding the construction of the sensor system 10, the sensor body 12 may be sealed such that no external liquids and/or gases may enter the inside of the sensor body. In addition, the sensor body 12 and flanges 16 and 18 may be made of materials such as stainless steel or other alloys compatible with possibly corrosive and/or harsh environments. Finally, any or all of the components of the sensor system 10 may be coated in accordance with embodiments described below to further enhance their properties.

Figure 2:
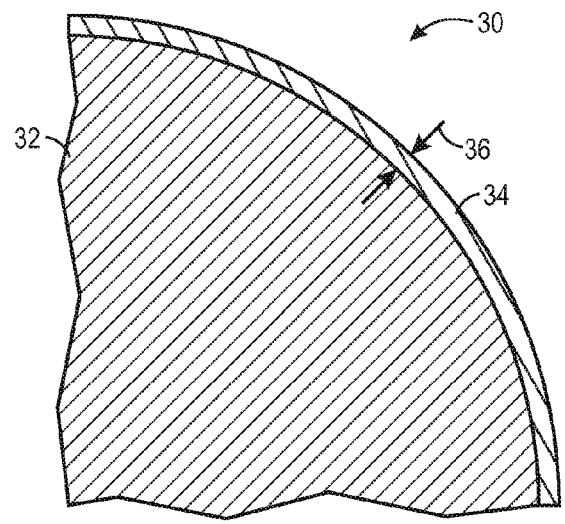
FIG. 2 is a cross sectional diagram of a portion of a sensor of FIG. 1, covered with an exemplary external coating.

For example, FIG. 2 is a cross section 30 of a portion of a sensor 32 with an external coating 34. As described below, the coating 34 may be applied such that no external surfaces of the sensor 32 are left uncoated, or could be selectively applied to certain surfaces or regions. For example, all external surfaces of certain proximity sensors may be coated, including, for example, the face 22 as shown in FIG. 1, because the coating 34 does not interfere with the operation of the proximity sensor. However, as the coating 34 may be opaque, an optical lens of certain photoelectric sensors may be left uncoated to enable transmission of light or other electromagnetic radiation through the optical lens. In addition, the thickness 36 of the coating 34 may be small compared to the diameter or thickness of sensor 32. For example, the thickness 36 of the coating 34 may be between approximately 50 micron and 75 micron. Certain embodiments of the coating 34 with thickness 36 may be durable enough to withstand years of repeated high-pressure washes.

Figure 3:
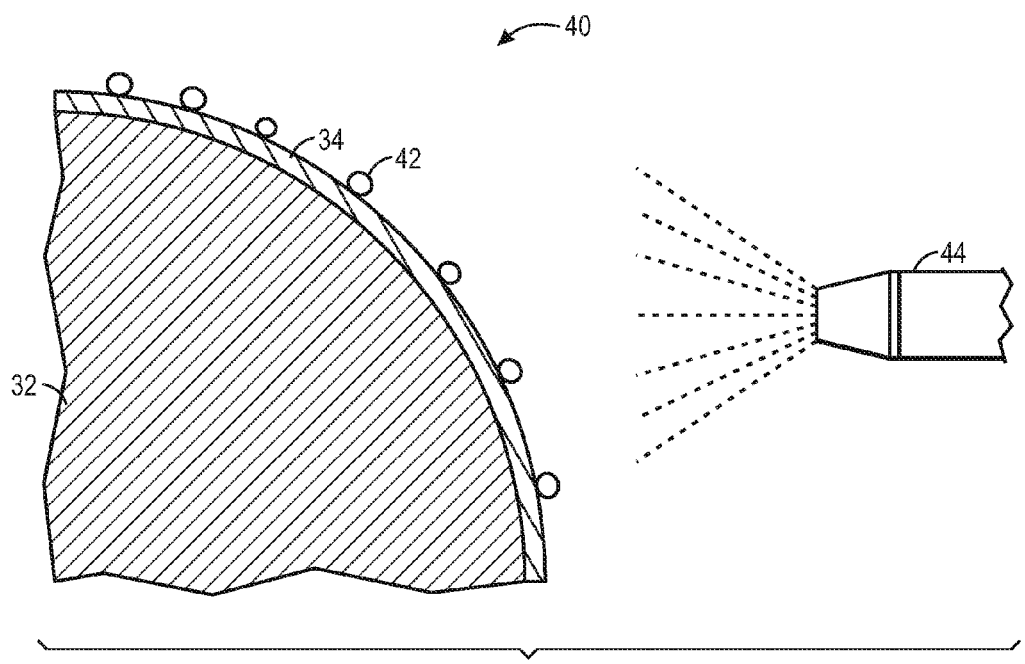
FIG. 3 is a cross sectional diagram of a portion of the same sensor covered with an exemplary external coating that is being washed.

In addition to durability, another beneficial property of certain embodiments of the coating is a low surface energy, which may result in a non-stick surface. For example, FIG. 3 shows a cross section 40 of a portion of the sensor 32 with the coating 34 being exposed to water. In particular embodiments, the surface energy of the coating 34 may be between approximately 15 dyne/cm and 35 dyne/cm. Because of this low surface energy, water sprayed onto the coating 34 may form small droplets 42 that easily run off the coating. The source of water may be a hose and nozzle 44 that accelerates the flow rate of the water. The water spray may easily remove any debris, dust, microorganisms, and/or biofilm on the surface of the coating 34 because of the low surface energy of the coating.

Figure 4:
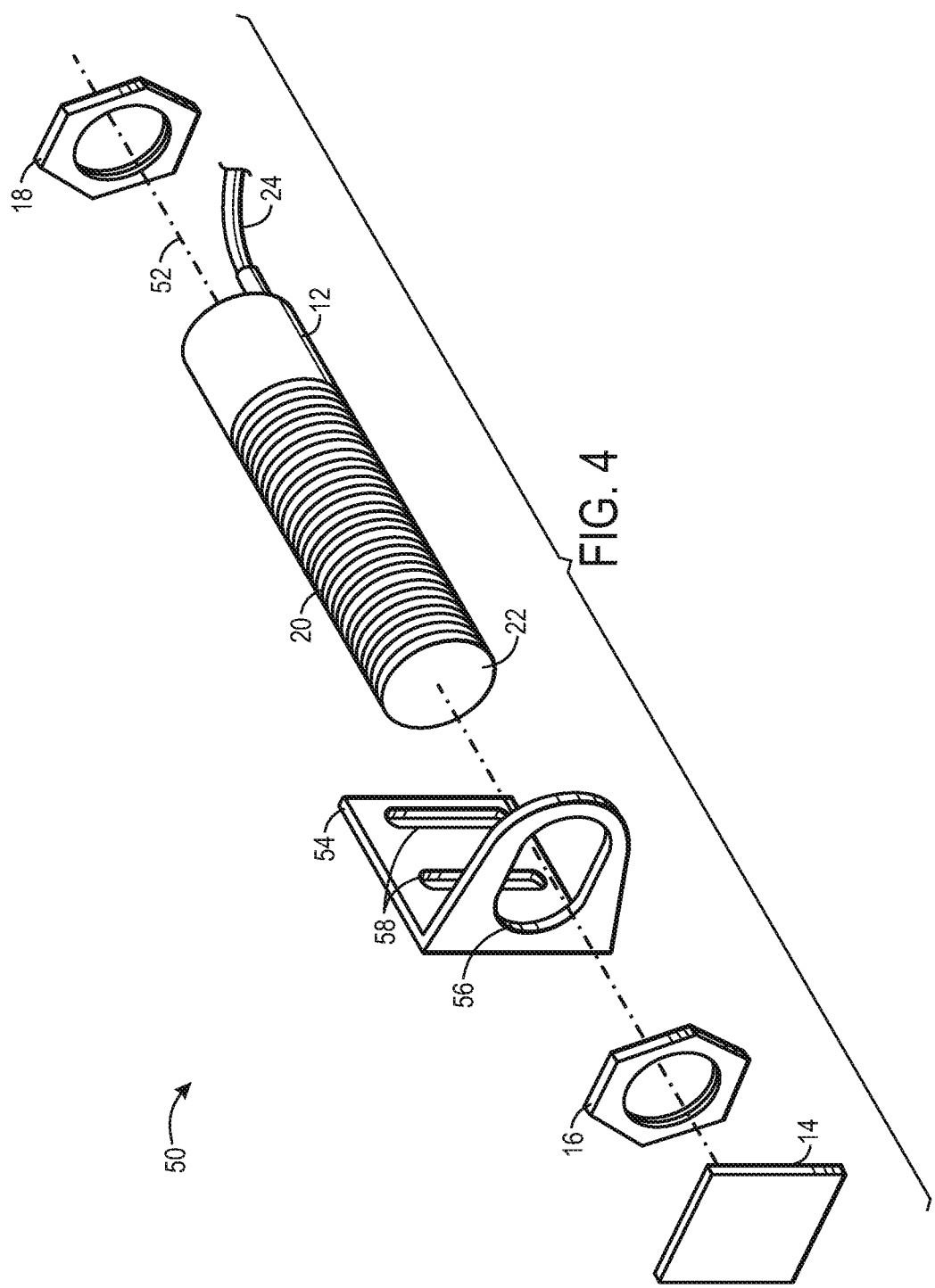
FIG. 4 is an exploded perspective diagram of an installed sensor system of the type shown in the previous figures, with various components covered with an exemplary external coating.

Not only may sensors and other industrial automation devices be coated, but mounting hardware, enclosures, and other components may be protected by a coating as well. For example, FIG. 4 is an exploded perspective diagram 50 of an installed sensor. Elements in common with those shown in FIG. 1 are labeled with the same reference numerals. In addition, an axis 52 is shown passing through the centers of all the components between the target 14 and the mounting flange 18. The sensor body 12 is installed using mounting bracket 54, which may be of a right-angle style with an oblong hole 56 for the sensor body to pass through and oblong holes 58 for mounting bolts to pass through. The oblong holes 56 and 58 facilitate installation by providing some flexibility in the arrangement of the bracket 54, sensor body 12, and bolts. Some or all of the surfaces of elements 12, 14, 16, 18, and 54 may be covered according to embodiments described below. Thus, complete coverage by the coating may offer few or no crevices, surfaces, or interstices in which microorganisms can remain and reproduce.

Before applying the coating to the sensor or other equipment, the coating is prepared or manufactured. FIG. 5 is a flowchart 70 of an exemplary method for preparing a non-stick, water-based (aqueous), antimicrobial coating. The first step 72 involves preparation of an acid mixture, which may include sulfuric and nitric acids. The two acids are mixed together at a ratio of sulfuric acid to nitric acid of approximately 3:1, which results in a solution with a pH of approximately 0. In the next step 74, graphite is soaked in the acid mixture. The graphite to be used may be any commercially available graphite, such as that available from the Sigma-Aldrich Company of St. Louis, Mo., that is at least approximately 95 percent or, more specifically, 99 percent graphite. The graphite particle sizes may be between approximately 1 micron and 100 micron or, more specifically, between 2 micron and 20 micron. Smaller graphite particle sizes may be difficult to obtain and unnecessary for this application, while larger sizes may inhibit the formation of a smooth coating.

After adding the graphite to the acid mixture, the graphite may continue to soak for at least approximately 48 hours. Acidifying the graphite enables thick, crack-free PTFE-based coatings. This allows single step preparation of coatings of desired thickness. In addition, acidified graphite is harder and more durable than non-acidified graphite. For example, the pencil hardness of certain embodiments may be greater than approximately 3H because of the addition of acidified graphite. Therefore, such disclosed embodiments may be able to resist scratches better than PTFE alone. Next, the acid mixture is separated from the graphite in step 76. This may be accomplished by straining the graphite to remove most of the acid mixture. Using this strained graphite, then, a graphite slurry consisting of approximately 10 percent graphite and 90 percent water is prepared.

After the acidified graphite slurry has been prepared, the slurry is added to a PTFE dispersion in step 78. The PTFE dispersion may be any commercially available aqueous dispersion, such as DuPont™ Teflon® PTFE TE-3859 or DuPont™ Teflon® PTFE TE-3893. Such aqueous dispersions, or suspensions, may consist of approximately 60 percent PTFE resin particles suspended in water and approximately 6 percent of a nonionic wetting agent and stabilizer. The PTFE particle sizes may be between approximately 0.05 micron to 0.5 micron. The nominal pH of the suspension may be approximately 10.5. In addition, suspensions similar to commercially available ones may be prepared by combining individual components with similar properties and compositions. For example, in one embodiment, the suspension may include approximately 40 percent to 75 percent or, more specifically, 50 percent to 60 percent PTFE resin particles suspended in water. The PTFE particle sizes may be between approximately 0.02 micron to 0.75 micron or, more specifically, between 0.05 micron to 0.5 micron. A base may be added to the suspension to improve the stability of the suspension and discourage growth of bacteria during storage. Returning to step 78, the acidified graphite slurry is added to the PTFE suspension dropwise, while the mixture is continually stirred. If the acidified graphite slurry is added too quickly to the PTFE suspension, which is basic, the residual acid in the slurry may cause the PTFE particles to precipitate out. Such a non-homogenous mixture may result in an uneven coating. The ratio of the PTFE suspension to the acidified graphite slurry may be approximately 5:1.

In the last step 80 of coating preparation, microporous particles doped with silver ions are added to the mixture of acidified graphite and PTFE suspension. Microporous particles may have pores with diameters of less than approximately 2 nm. Examples of microporous particles include, but are not limited to, zeolites and zeolite-like materials, pillared materials, clathrasils and clathrates, carbon molecular sieves, organic/inorganic porous hybrid materials, and porous metal oxides. Zeolites include both naturally occurring and man-made minerals and are characterized by an open, porous structure. The pores may have different shapes and sizes, making them suitable for accommodating a variety of cations. In one embodiment, a zeolite with pores shaped like cubes with sides of length of approximately 1 micron and pores of approximately 5 angstrom to 50 angstrom or, more specifically, 10 angstrom to 20 angstrom may be used. Such a zeolite may be suitable for accommodating silver cations, which have an ionic diameter of approximately 2.5 angstrom, and excluding graphite particles, which may be as small as approximately 20,000 angstrom.

Examples of commercially available silver ion doped zeolites which possess the properties described above include, but are not limited to, AlphaSan® RC 2000 (with 10 percent silver by weight) and AlphaSan® RC 5000 (with 3.8 percent silver by weight). Other microporous materials doped with at least 2 percent silver by weight, or more specifically, 3 percent silver by weight may be used as long as enough silver is present so that the coating has effective antimicrobial properties. Silver is used in antimicrobial compositions because when microorganisms encounter silver ions, the microorganisms die because silver ions may interfere with respiration, cell division, and/or metabolism. In one embodiment, an ion exchange occurs that replaces the silver ion in the zeolite with a sodium ion naturally present in water. The silver ion kills the microorganism and together both are washed away later as will be described below. Thus, a small number of silver ions are consumed during the life of the coating, depending on the number of microorganisms that contact the coating. As an example of the antimicrobial properties of the coating, stainless steel coated in accordance with an embodiment of the present technique exhibits an approximately 4 log to 5 log greater kill rate of *Escherichia coli* and *Staphylococcus aureus* after 24 hours compared to bare stainless steel using American Association of Textile Chemists and Colorists (AATCC) test method 174. Returning to step 80, the silver ion doped zeolite may be added directly to the mixture of acidified graphite and PTFE dispersion and mixed well to achieve a homogenous mixture. Such a mixture is stable for at least approximately 48 hours and may be stored at room temperature. The ratio of the acidified graphite to the zeolite may be approximately 10:1.

Once the coating has been prepared by the method described above, the coating may be applied to a surface. FIG. 6 is a flowchart 90 of an exemplary method for applying the non-stick, water-based, antimicrobial coating to a surface of an object according to one embodiment. The coating process may be performed at room temperature. In an exemplary embodiment, the first step 92 involves preparing the surface to be coated by roughening the surface, where needed, to enhance the bond between the surface and the coating. For embodiments where metals, such as stainless steel, are coated, roughening may be accomplished by sandblasting the surface. For embodiments involving softer materials, such as plastics, rubbing the surface with sandpaper may be sufficient. For selected substrates, no primer is necessary and the coating may be applied directly to the roughened surface in a single step. In the next step 94 of the method, the coating is thoroughly mixed until the coating is homogeneous. Next, the coating is applied to the surface in step 96. A variety of application methods may be used, including, but not limited to, spraying, dipping, brushing, web coating, and calendaring. The thickness of the applied coating may be between approximately 35 micron to 90 micron or, more specifically, between 50 micron to 75 micron. Thicker coats may be susceptible to cracking during drying and thinner coats may not cover evenly and completely all portions of the surface. After application, the coating may be allowed to dry in step 98 for at least approximately 2 hours at room temperature. Because no volatile organic compounds (VOCs) are used in the coating, no VOCs are given off during the drying process. This may be advantageous in enclosed spaces, where people may be in close proximity to the coating, or to reduce the amount of VOCs released into the atmosphere.

After the coating has been applied and allowed to dry, the coating is cured in an oven in step 100. In one embodiment, the coated object is placed in the oven and the temperature is increased to at least approximately 330 degrees Celsius at a rate of approximately 20 degrees Celsius/minute and held there for at least approximately 10 minutes before removing the object for cooling. The atmosphere in the oven may be air. Alternatively, a nitrogen atmosphere may be used because the nonionic wetting agent and stabilizer are driven off better in the absence of oxygen. In addition, in certain embodiments, the coating is cured at a temperature greater than approximately 330 degrees Celsius to produce a continuous, smooth, and even appearance for the coating. Such an appearance is produced because the PTFE particles melt at a lower temperature of approximately 320 degrees Celsius. Moreover, the relatively high melting point of the PTFE imparts good high temperature resistance to the cured coating. Finally, although a single 50 micron to 75 micron thick coating may be sufficient, if a thicker coating is desired, steps 96 through 100 may be repeated as many times as necessary.

Once the coating on the object has cured, the object may be placed into service. For example, proximity sensors may be used in the food processing industry to detect the presence of nearby objects without physical contact. During use, sensors may become exposed to food residues and possibly microorganisms. The antimicrobial features of particular embodiments of the coating described above may kill various microorganisms that may be exposed to the sensor. Later, the sensor may be cleaned and sanitized, as is typical for much of the equipment used in the food processing industry. Such cleaning is often scheduled for at least once per day. During cleaning, water and other cleaning agents may be directed at the sensor, often at high pressure. During this process, the low surface energy of particular embodiments of the coating may facilitate removal of food residues and dead microorganisms. Once cleaned, the non-stick and antimicrobial features of the coating remain largely intact. Simulations of daily high-pressure cleanings using water at approximately 1200 psi and 60 degrees Celsius demonstrate that the coating maintains good adhesion to the substrate and withstands peeling and cracking. Over time, the exposure of the coating to water and certain other cleaning agents, depending on chemical composition and concentration, may result in the concentration of silver ions at the surface of the coating being reduced enough to warrant reactivation.

To reactivate the non-stick, water-based, antimicrobial coating, the exemplary method shown in the flowchart 110 of FIG. 7 may be used. The first step 112 involves applying certain acids such as, but not limited to, nitric acid or acetic acid to the surface of the coating. Other acids that result in silver salts with high solubility in water may also be used. In one exemplary approach, about 1 molar nitric acid is brought into contact with the surface of the coating. The nitric acid may be applied using a variety of methods, not limited to, dipping, wiping, sponging, and spraying. In the next step 114, the acid remains in contact with the coating for at least about 5 minutes. While the exact method of working is not known, one possible explanation is that the acidic environment created by the nitric acid causes silver ions in zeolite pores deeper in the coating to migrate to zeolite pores closer to the surface. After about 5 minutes, the concentration of silver ions at or near the surface is about the same as when the coating was first applied. No additional silver is added during the process. Instead, a reversal of the ion exchange that occurs during microbe death occurs. In other words, sodium ions leave the zeolite closest to the surface and are replaced with silver ions from zeolite deeper in the coating. A very large number of silver ions are present in the zeolite of the coating initially, and only a relatively small number are lost over time. Thus, enough silver ions are present in zeolite deeper in the coating to replace the silver ions lost killing microorganisms. Next, the acid is removed from the surface in step 116. This may be accomplished by evaporation of the acid or removal by a water wash. At this point, the capabilities of the coating have been renewed to be about the same as that of a newly cured coating and the coated object may be placed back in service.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A coated industrial automation device, comprising:
an industrial automation device, wherein the industrial automation device comprises a device in the food and beverage industry subject to high pressure washes, and is selected from the group consisting of photoelectric sensors, encoders, limit switches, controllers, push buttons, and cordsets;
an antimicrobial coating covering a surface of the industrial automation device, wherein the coating comprises acidified graphite particles, polytetrafluoroethylene resin particles, and silver ion doped microporous particles.

2. The coated industrial automation device of claim 1, wherein the industrial automation device comprises stainless steel, plastic, or any combination thereof 3. The coated industrial automation device of claim 1, wherein the industrial automation device comprises a sensor.

4. The coated industrial automation device of claim 1, wherein the industrial automation device comprises a lens, wherein the lens is not covered by the antimicrobial coating.

5. The coated industrial automation device of claim 1, wherein the silver ion doped microporous particles comprise pores with a diameter less than about 30 angstrom.

6. The coated industrial automation device of claim 5, wherein most of the acidified graphite particles comprise a diameter of less than about 20 micron, whereby the acidified graphite particles cannot enter into the pores of the silver ion doped microporous particles.

7. The coated industrial automation device of claim 5, wherein the acidified graphite particles comprise diameters of about 2 micron to 20 micron.

8. The coated industrial automation device of claim 1, wherein the polytetrafluoroethylene resin particles comprise particles with a diameter of about 0.05 micron to 0.5 micron.

9. The coated industrial automation device of claim 1, wherein the silver ion doped microporous particles comprise greater than about 3 percent silver ion by weight.

10. The coated industrial automation device of claim 1, wherein the antimicrobial coating comprises a thickness of about 50 micron to 75 micron.

11. The coated industrial automation device of claim 1, wherein the industrial automation device additionally comprises a sensor, enclosure, mounting hardware, bracket, controller, push button, cordset, or any combination thereof.

12. The coated industrial automation device of claim 1, wherein the surface of the industrial automation device is roughened prior to covering with the antimicrobial coating.

13. The coated industrial automation device of claim 1, wherein the silver ion doped microporous particles comprise zeolite.

14. A coated industrial automation sensor, comprising:
an industrial automation sensor, wherein the industrial automation sensor comprises a sensor in the food and beverage industry subject to high pressure washes, and is selected from the group consisting of photoelectric sensors, encoders, and limit switches;
an antimicrobial coating covering a surface of the industrial automation sensor, wherein the coating comprises acidified graphite particles, polytetrafluoroethylene resin particles, and silver ion doped microporous particles.

15. The coated industrial automation sensor of claim 14, wherein the industrial automation sensor comprises stainless steel, plastic, or any combination thereof.

16. The coated industrial automation sensor of claim 14, wherein a lens of the industrial automation sensor is not covered by the antimicrobial coating.

17. The coated industrial automation sensor of claim 14, wherein the silver ion doped microporous particles comprise pores with a diameter less than about 30 angstrom.

18. The coated industrial automation sensor of claim 17, wherein most of the acidified graphite particles comprise a diameter of less than about 20 micron, whereby the acidified graphite particles cannot enter into the pores of the silver ion doped microporous particles.

19. The coated industrial automation sensor of claim 17, wherein the acidified graphite particles comprise diameters of about 2 micron to 20 micron.

20. The coated industrial automation sensor of claim 14, wherein the polytetrafluoroethylene resin particles comprise particles with a diameter of about 0.05 micron to 0.5 micron.

21. The coated industrial automation sensor of claim 14, wherein the silver ion doped microporous particles comprise greater than about 3 percent silver ion by weight.

22. The coated industrial automation sensor of claim 14, wherein the antimicrobial coating comprises a thickness of about 50 micron to 75 micron.

23. The coated industrial automation sensor of claim 14, wherein the surface of the industrial automation sensor is roughened prior to covering with the antimicrobial coating.

24. The coated industrial automation sensor of claim 14, wherein the silver ion doped microporous particles comprise zeolite.

* * * * *